(12) United States Patent
Pistorino et al.

(10) Patent No.: US 8,304,244 B2
(45) Date of Patent: *Nov. 6, 2012

(54) HEMOGLOBIN BASED BILIRUBIN REFERENCE MATERIAL

(75) Inventors: Michael Pistorino, Groton, MA (US); Prasad Pamidi, Billerica, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/349,640

(22) Filed: Jan. 13, 2012

(65) Prior Publication Data

US 2012/0104323 A1    May 3, 2012

Related U.S. Application Data

(63) Continuation of application No. 12/432,448, filed on Apr. 29, 2009, now Pat. No. 8,119,407.

(60) Provisional application No. 61/049,197, filed on Apr. 30, 2008.

(51) Int. Cl.
*G01N 33/72* (2006.01)

(52) U.S. Cl. ........... 436/15; 436/8; 436/12; 436/63; 436/66; 436/97; 436/164; 436/166; 252/408.1

(58) Field of Classification Search ............ 436/8, 12, 436/15, 63, 66, 86, 87, 88, 97, 164, 166, 436/171, 174; 252/408.1; 422/73, 82.05, 422/82.09
See application file for complete search history.

(56) References Cited

U.S. PATENT DOCUMENTS

| | | | |
|---|---|---|---|
| 4,485,174 A | 11/1984 | Chiang et al. | |
| 5,278,073 A | 1/1994 | Grandjean | |
| 5,310,679 A | 5/1994 | Artiss et al. | |
| 5,384,248 A | 1/1995 | Sakata et al. | |
| 5,591,400 A | 1/1997 | Dektar et al. | |
| 5,637,505 A | 6/1997 | Li et al. | |
| 5,891,730 A | 4/1999 | Li et al. | |
| 6,372,503 B1 | 4/2002 | Samsoondar | |
| 6,980,285 B1 | 12/2005 | Hansen et al. | |
| 8,119,407 B2 * | 2/2012 | Pistorino et al. | 436/15 |
| 2004/0072359 A1 | 4/2004 | Southard | |
| 2004/0121476 A1 | 6/2004 | Samsoondar | |
| 2009/0088340 A1 | 4/2009 | Summers | |

FOREIGN PATENT DOCUMENTS

WO    WO2008006152    1/2008

OTHER PUBLICATIONS

Written Opinion of the International Searching Authority for PCT/US09/42112, Jul. 20, 2009.
Extended European Search Report, including Supplemental European Search Report, issued in a counterpart European patent application No. 09739689, mailed on Sep. 5, 2011, 5 pages.
International Preliminary Report on Patentability for PCT/US2009/042112 issued on Nov. 2, 2010.
International Search Report dated Jul. 27, 2009, received in PCT/US2009/042112.
Non-Final Office Action mailed from the USPTO on May 18, 2011, for U.S. Appl. No. 12/432,448.

* cited by examiner

*Primary Examiner* — Maureen Wallenhorst
(74) *Attorney, Agent, or Firm* — Burns & Levinson LLP

(57) ABSTRACT

What is described is a single reference material and method of making useful for calibrating or qualifying instruments that are diagnostic spectroscopically for bilirubin, hemoglobin, and hemoglobin fractions, and, optionally, diagnostic for other blood analytes by sensor means.

20 Claims, 3 Drawing Sheets

HEMOGLOBIN BASED BILIRUBIN REFERENCE MATERIAL

RELATED APPLICATIONS

This application is a continuation application of U.S. patent application Ser. No. 12/432,448, filed on Apr. 29, 2009, now U.S. Pat. No. 8,119,407 issued on Feb. 21, 2012 which claims priority to U.S. provisional patent application Ser. No. 61/049,197, filed Apr. 30, 2008, the entire contents of each are incorporated herein by reference.

FIELD OF INVENTION

This invention relates to blood-based reference materials useful for calibrating or qualifying instrument systems for total bilirubin, total hemoglobin and hemoglobin fractions using spectroscopic measurements. Further, the invention may be used in instruments that have, in addition to CO-Oximetry capabilities, sensors such as electrochemical or enzymatic sensors for measuring pH, blood gasses, e.g., $PO_2$ and $PCO_2$, and other blood analytes including electrolytes and metabolites.

BACKGROUND OF THE INVENTION

Determination by automated instrumentation of blood, pH, $PO_2$, $PCO_2$, electrolytes, metabolites and CO-Oximetry fractions are routine clinical laboratory analyses. CO-Oximeter instruments typically measure total hemoglobin concentration (tHb), and hemoglobin fractions e.g., oxyhemoglobin ($O_2$Hb), methemoglobin (MetHb), carboxyhemoglobin (COHb), sulfhemoglobin (SHb), and deoxyhemoglobin (HHb). These fractions are referred to as CO-Ox fractions or hemoglobin fractions or hemoglobin derivatives. Currently available instruments such as IL 682 and GEM® Premier™ 4000 (Instrumentation Laboratory Company, Bedford, Mass.) have the ability to measure blood pH, gases, electrolytes, metabolites, total bilirubin, and/or total hemoglobin and hemoglobin fractions in the same instrument.

Blood hemoglobin and hemoglobin fractions absorb visible light within the wavelength range of 450-700 nm. For example, a normal oxygenated blood spectrum has two main peak wavelengths at 542 and 578 nm and absorbance rapidly decreases close to zero at wavelengths greater than 610 nm.

Based on the known hemoglobin fraction wavelength regions and the known relationship between hemoglobin concentration and absorbance spectrum, CO-Oximeters analyze blood samples by comparing the sample absorbance spectrum to an instrument calibration set consisting of hemoglobin spectra of known concentrations (FIG. 1) of each individual fraction. The data are analyzed by multicomponent analysis to calculate the concentrations of total hemoglobin and each hemoglobin fraction present in a patient's blood sample.

Reference materials generally function to validate the performance of a diagnostic instrument, such as a CO-Oximeter. These materials are typically aqueous or blood-based materials. As used herein, blood-based materials are materials derived from human or animal blood that include some component of red blood cells, but not referring to plasma or serum materials without some component of red blood cells. The blood-based materials allow for the direct match of the spectrum of blood. However, there are no blood-based quality control (QC) or reference materials available that include both hemoglobin fractions and bilirubin due to limited useful shelf-life caused by, for example, instability of bilirubin and/or bilirubin. Traditionally, bilirubin is validated using plasma or serum based reference materials that do not include hemoglobin. Therefore, reference materials for bilirubin on whole/lysed blood CO-Oximetry systems are limited in their ability to establish corrections for hemoglobin interference due to the lack of bilirubin reference materials that include hemoglobin and hemoglobin fractions.

Bilirubin, a principal component of bile pigment in a body fluid such as blood, is produced by the decomposition of heme from hemoglobin in red blood cells (RBCs). Two main fractions of bilirubin are present in blood. One is free or unconjugated bilirubin (indirect) and the other is conjugated (direct) bilirubin. Conjugated bilirubin is chemically bound to glucuronic acid to render water solubility of bilirubin for excretion from the body.

Increased serum bilirubin levels, a combination of direct/conjugated and indirect/unconjugated bilirubin, produce the clinical condition known as jaundice. The liver converts bilirubin to conjugated bilirubin so that it is excreted from the body. In obstructive jaundice and in liver disease, excretion or metabolism is impaired and an elevated conjugated bilirubin fraction occurs. This form of jaundice differs from the cause of neonatal jaundice. The liver of newborns is not fully developed at birth, and newborns often lack the enzymes necessary to convert the unconjugated form to the conjugated form of bilirubin for excretion. Increased indirect bilirubin is an important measurement for newborns.

Traditional clinical laboratory measurements to assay total bilirubin in blood use the Jendrassik-Gróf principle, where all bilirubin species react with diazonated sulfanilic acid, in the presence of caffeine-benzoate acting as a promoter, to yield a red azopyrole. On addition of alkaline tartrate to serum or plasma, the color turns blue, which has a maximum absorbance at 598 nm. A disadvantage of this prior art method is that it cannot be completed using whole blood. Serum or plasma must be used, which requires separation from cellular blood components, typically by centrifugation, before measurement. More recently, methods have been developed whereby bilirubin is measured via direct spectrophotometry on whole blood using analytical instruments, for example, the GEM Premier 4000 cartridge-based system (Instrumentation Laboratory Company, Bedford, Mass.) or the IL Synthesis (Instrumentation Laboratory Company, Bedford, Mass.).

The increasing popularity of the use of direct spectrophotometry in clinical laboratories can be attributed to ease of use, speed of results, and convenience. These systems measure whole blood, thereby eliminating the time required to separate blood formed elements from plasma or serum, using spectrometric measurements to quantify bilirubin, total hemoglobin concentration (tHb), and the hemoglobin fractions $O_2$Hb, COHb, SHb, and MetHb, i.e., the CO-Ox fractions, and are often coupled to electrochemical sensors to quantify other analytes of interest. Some clinical analyzers only report on a portion of these analytes. CO-Oximeters often lyse RBCs by chemical means, mechanical means, or both, to reduce scattering effects of cell membranes and to improve overall accuracy of the measuring system by reducing the background noise.

Bilirubin, unlike many other blood constituents, is highly unstable in many reference materials because it is sensitive to light, oxygen, and ambient temperatures. For this reason bilirubin based reference materials typically require refrigerated or frozen storage conditions. In the presence of either light, elevated temperature, or oxygen, the conversion of bilirubin to biliverdin, an analyte which has a very different spectral absorbance than bilirubin, is accelerated. For example, in current blood-based reference materials, such as those disclosed in U.S. Pat. No. 4,485,174 i.e., blood-based materials that contain hemoglobin, oxygen is required in order to provide stable, clinically meaningful levels of oxyhemoglobin, the primary fraction of total hemoglobin. The presence of oxygen accelerates the conversion of bilirubin to biliverdin. To minimize the effect of bilirubin's instability, i.e., the conversion of bilirubin to a compound, such as biliverdin, having a different absorbance, prior art reference materials for bilirubin, e.g., those used for CAP NB-surveys, are typically dispensed in vials and stored frozen. This storage method is unsatisfactory because it increases measurement variability due to rigorous handling procedures and provides an opportunity for pre-analytical error. Furthermore, these materials do not provide for measurement of total hemoglobin and/or hemoglobin fractions together with bilirubin in the same reference material in which the quantities of these analytes relate to meaningful clinical levels. Freezing and thawing, as required for many bilirubin reference materials, is unsatisfactory for hemoglobin based reference materials. The risk of an inaccurate measurement is elevated when hemoglobin is measured after freezing because the temperature change may induce conversion of oxyhemoglobin to methemoglobin.

At present, because of the instability of solutions containing bilirubin stored at refrigerated temperatures and the instability of hemoglobin materials upon freezing and thawing, a single blood based quality control or reference material for clinically meaningful concentrations of bilirubin, total hemoglobin, and its fractions, has not been developed. Organic dye based colored materials are in use by some manufacturers to simulate the spectral properties of hemoglobin and bilirubin assays. Such dye based products are useful for general quality check of the optical systems but are not very specific in qualifying or identifying performance quality issues. In addition, dye based quality materials require manufacturer-specific secondary correction factors or analytical algorithms separate from those used to analyze clinical samples to report clinically meaningful hemoglobin or bilirubin results. For this reason, a single blood based reference material, i.e. a blood-based material other than plasma or serum, that provides clinically relevant measurements of both hemoglobin and bilirubin independent of manufacturer or analytical system has a potential for clinical and commercial interest.

In other words, in spite of the efficiency in qualifying and calibrating instrument systems that would be provided by such a single reference material and the long felt commercial need for such a product, a single blood based reference material providing clinically relevant concentrations of bilirubin, hemoglobin and its fractions, without requiring instrument platform-specific secondary correction factors or analytical algorithms, is not available.

Currently, two separate materials are required for calibrating or running quality control on bilirubin, total hemoglobin, and hemoglobin fractions; one for bilirubin and one for total hemoglobin and hemoglobin fractions. Accordingly, the laboratory time required for conducting quality control on bilirubin and hemoglobin is longer than would be required with a single reference material that includes bilirubin, total hemoglobin, and hemoglobin fractions. In addition, evaluation of bilirubin in the presence of clinically relevant concentrations of hemoglobin provides more accurate corrections for hemoglobin interference on bilirubin, and a more accurate evaluation of an analyzer's ability to accurately measure these analytes in patient samples.

SUMMARY OF THE INVENTION

The invention relates to compositions, methods of making, and methods of using the composition for quality control of an analytical instrument for measurement of bilirubin, total hemoglobin, and hemoglobin fractions and, optionally, other analytes of interest in body fluids. The embodiments of the invention have the following features in common, a reference material including a blood-based material that has predetermined quantities of the analytes hemoglobin and/or hemoglobin fractions, and one or more dyes that mimic the absorbance spectra of bilirubin. The invention is useful as a reference material for each of these analytes across a plurality of instrument models from multiple manufacturers.

In one aspect, the invention relates to a reference material having at least the following features, (i) at least one component obtained from blood; and (ii) one or more dyes having an absorbance spectrum similar to bilirubin concentrations at pre-determined clinically relevant levels. In one embodiment, at least one component obtained from blood comprises a pre-determined clinically relevant quantity of total hemoglobin and hemoglobin fractions.

Alternatively, the reference material according to the invention includes at least the following features, (i) at least one component obtained from blood; (ii) a pre-determined clinically relevant quantity of hemoglobin; and (iii) one or more dyes having an absorbance spectrum similar to bilirubin concentrations at pre-determined clinically relevant levels.

The reference material according to the invention includes one or more dyes, for example, chrysophenine, metanil yellow, flavianic acid and combinations thereof, for example. In one embodiment, the concentration of chrysophenine is less than about 1000 mg/L, the concentration of metanil yellow is less than about 1000 mg/L, and the concentration of flavianic acid is less than about 500 mg/L. The reference material further includes hemoglobin and hemoglobin fractions at pre-determined levels that mimic levels that are found in the body fluids of patients. In one embodiment, the hemoglobin fractions are oxyhemoglobin, methemoglobin, deoxyhemoglobin, carboxyhemoglobin, and/or sulfhemoglobin. In one embodiment, according to the invention, the at least one component obtained from blood is sourced from red blood cells. The reference material is stable at 0-40° C. for at least 2, 6, or 12 months or more.

In one embodiment, according to the invention, the reference material further includes a surfactant, such as Brij® 35 (Polyoxyethylene (23) lauryl ether), Brij® 700 (Polyoxyethylene (100) stearyl ether), Arlatone® G (polyoxyethylene fatty glyceride), or Triton® X-100 (Polyethylene glycol tert-octylphenyl ether), for example.

In another embodiment, according to the invention, the reference material further includes a protein, such as albumin. In a particular embodiment, the concentration of albumin in the reference material is a concentration that is different than albumin concentrations found in a patient body fluid.

In another aspect, the invention relates to a method for quality control of an instrument, for example, a clinical analyzer that is capable of measuring bilirubin, total hemoglobin, and hemoglobin fractions. In one embodiment the method steps include (i) introducing into the analyzer a quality control standard material comprising a pre-determined clinically relevant quantity of hemoglobin, and one or more dyes having an absorbance spectrum similar to bilirubin concentrations at predetermined clinical levels, (ii) obtaining an analyzer analysis of the control standard material for hemoglobin and/or bilirubin concentrations, and (iii) comparing the analyzer analysis of the hemoglobin concentration or bilirubin concentration with the pre-determined concentrations of the total hemoglobin and/or total bilirubin. In one embodiment, the method further includes pre-dissolving the one or more dyes in a surfactant and/or protein solutions, for example in a solution including Brij 35® and albumin. The Brij 35® concentration in the solution may be in the range of about 100-1500 g/L in water, or about 800-1000 g/L in water. The albumin concentration in the solution may be in the range of about 1-100 g/L in water, or about 45-55 g/L in water. In one embodiment, pre-dissolving the one or more dyes in a surfactant-containing, protein-containing, or a protein/surfactant-containing solution occurs before dissolving the one or more dyes in a solution including hemoglobin. The method according to the invention further requires that the one or more of the dyes do not interfere with the analysis of total hemoglobin or fractions of hemoglobin.

BRIEF DESCRIPTION OF THE DRAWINGS

The invention is described in more detail below with reference to the following figures, wherein.

DESCRIPTION OF THE INVENTION

Figure 1:
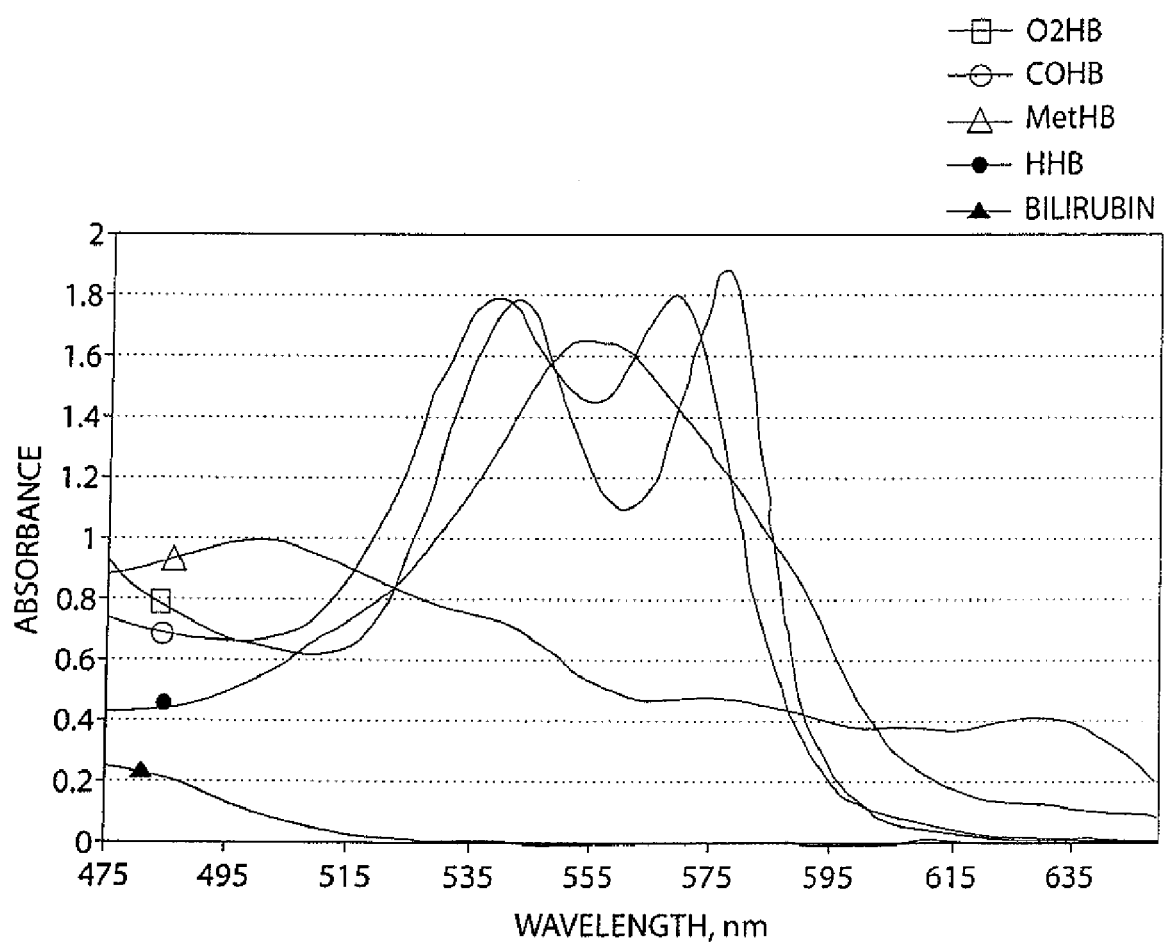
FIG. 1 illustrates the spectra of the 4 primary hemoglobin fractions and bilirubin in plasma not in the presence of hemoglobin.

The present invention provides a single blood-based quality control standard reference material and method of making and using which, in the presence of hemoglobin and hemoglobin fractions in blood, mimics the spectrum of bilirubin when the single reference material is used in an analytical instrument capable of CO-Oximetry.

The problem solved by the invention disclosed herein is making a reference material for bilirubin, total hemoglobin, and hemoglobin fractions as a single material such as a single solution that is useful for measuring clinically relevant quantities of bilirubin, total hemoglobin, and hemoglobin fractions in CO-Oximeters on a variety of instrument platforms and/or manufactured by more than one company.

As used herein, a clinically relevant reference material may contain a combination of total hemoglobin, hemoglobin fractions, and/or bilirubin in the following concentration ranges (Table I).

TABLE I

| Target Analyte Ranges for Final Products (HHb = balance) | | | | | |
|---|---|---|---|---|---|
| | tHb g dL$^{-1}$ | O$_2$Hb % | COHb % | MetHb % | tBil mg dL$^{-1}$ |
| Total Range | 0-25 | 0-100 | 0-100 | 0-100 | 0-40 |
| Physiological Ranges | 8-20 | 60-98 | 0-20 | 0-20 | 0-30 |
| Normal Range | 14-17 (Male) 12-15 (Female) | 94-98 | 0-3 (non-smoker) | 0-3 | 0-2 |

The problem solved by the invention relates to a reference material and method of making for (i) the analytes bilirubin, total hemoglobin, and hemoglobin fractions, at (ii) clinically meaningful analyte concentrations that are included in (iii) one reference material, (iv) suitable for serving as a qualifying or calibrating quality control standard for bilirubin, total hemoglobin and hemoglobin fractions. Until the present invention, clinically relevant quantities could be achieved in standard reference materials for bilirubin, total hemoglobin and hemoglobin fractions only if bilirubin was provided without clinically relevant quantities of hemoglobin in one reference material and hemoglobin and hemoglobin fractions were provided without clinically relevant quantities of bilirubin in another reference material. A single reference material that combined dye and blood-based materials to mimic clinically relevant concentrations of bilirubin, total hemoglobin, and hemoglobin fractions was not known.

The present invention solves many problems not solved by prior art quality control standard reference material for bilirubin, total hemoglobin and hemoglobin fractions, despite the long-felt commercial need for this material. Among the problems solved by the current invention is the identification of compounds with bilirubin-like absorbance patterns for spectrophotometric scan based measurement. Additional problems solved by the present invention include:

interference with measurement of tHb and CO-Ox fractions;

solubility limitations;

storage stability limitations;

high manufacturing costs;

incompatibility or inaccuracy on some instrument platforms due to the inability to match the spectrum of the bilirubin and the magnitude of the bilirubin signal in a background of hemoglobin noise;

incompatibility with some sensors, by inducing excessive signal drift, for example; and the necessity for multiple reference materials to provide clinically relevant concentrations of total hemoglobin, hemoglobin fractions, and bilirubin.

Moreover, the present invention also solves the problem of providing a stable bilirubin absorbance while trying to formulate in a predictable manner a reference material in the presence of clinically relevant quantities of hemoglobin for analytical systems for the detection of blood analytes that utilize spectrophotometric analysis, optionally, in combination with electrochemical sensors.

The present invention resolves the long-felt commercial need for stable, blood based quality control standards for bilirubin, total hemoglobin and hemoglobin fractions all in one reference material with a commercially practical shelf life that provides pre-determined clinically meaningful concentrations of these analytes for quality control reference materials. The reference material according to the invention may be used for calibrating clinical analyzers, as a calibration or verification product, or as CAP (College of American Pathologists) instrument qualifying survey materials. The stable reference material according to the invention reduces the testing time and manufacturing costs by combining a bilirubin substitute with other analytes e.g., hemoglobin and CO-Ox fractions in a single reference material. Bilirubin stabilizing compounds used in prior art quality control standard materials such as ferrocyanide, EDTA, bilirubin analogs and biliverdin, destabilize hemoglobin fractions, provide insufficient stability in the presence of oxygen, and/or interfere with measurement of other CO-Ox fractions. The reference material according to the invention may also be used as an internal control to verify spectrometer performance for bilirubin, total hemoglobin, and hemoglobin fractions.

As used herein, stable means change of no more than 4% for bilirubin from the initial bilirubin concentration and no more than 3% for total hemoglobin from the initial total hemoglobin, when stored from 0-40° C.

Reference materials generally function to validate the performance of diagnostic instruments, for example, instruments with CO-Oximeters. The invention described herein includes formulations that span the concentration ranges of analytes which CO-Oximeters are typically designed to measure (Table I), which are broader than the ranges typically observed in patient samples.

Figure 2:
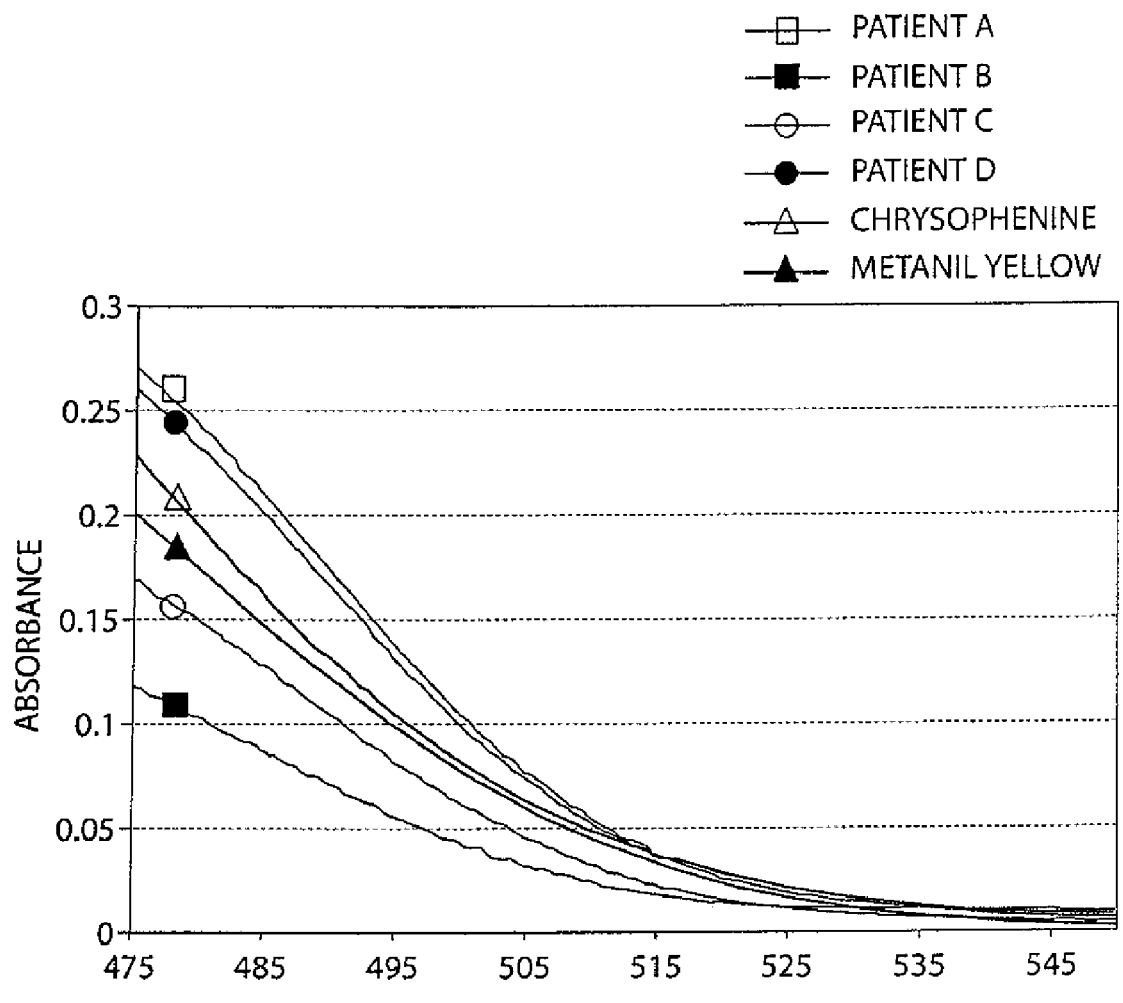
FIG. 2 illustrates the dye spectrum (without hemoglobin) as compared to patient bilirubin in plasma.

The present invention provides a quality control standard reference material and method of making, for measurements of bilirubin, total hemoglobin, and hemoglobin fractions. Typically, dye based products require instrument specific secondary correction factors for the system to generate meaningful clinical results for hemoglobin or bilirubin. According to the invention, one or more dyes are used to mimic the spectra of bilirubin, where standard blood calculations based on multicomponent analysis that are used to calculate bilirubin in clinical samples can be directly applied to predict the bilirubin equivalent value of the dye without application of any secondary correction factors. According to the invention, due to the spectral similarities of the dyes to bilirubin, no special secondary algorithms are needed to convert the dye measurements to a meaningful bilirubin result (FIG. 2). Moreover, according to the invention, hemoglobin derived from RBCS (blood-based) is utilized in combination with one or more dyes to make a single reference material for bilirubin, hemoglobin, and hemoglobin fractions, useful for calibrating or qualifying analytical instruments having CO-Oximetry capabilities. Utilization of hemoglobin is advantageous solving one problem in prior art reference materials by minimizing the known variability between instrument platforms when measuring total hemoglobin and hemoglobin fractions.

According to the invention, the reference material comprises one or more dyes that mimic the absorbance pattern of bilirubin while having negligible absorbance at wavelengths greater than 520 nm (FIG. 2). Significant absorbance at wavelengths greater than 520 nm is disadvantageous because it would interfere with the measurement of hemoglobin fractions defeating the advantages of the single reference material.

Additionally, in one embodiment according to the invention, in order to make the reference material, one or more dyes are pre-dissolved in a solution containing one or more proteins such as albumin, for example, bovine serum albumin (BSA) or human serum albumin (HSA) at, for example, room temperature and, optionally, one or more surfactants. Preliminary observations identified solubility limitations of the dyes when added directly to aqueous solutions, hemoglobin solutions, deionized water, or to solutions which only contained a protein, such as albumin, or a surfactant. Surprisingly, the addition of exogenous protein, i.e., proteins in addition to those native proteins found in patient body fluids, e.g., albumin in water, significantly increased the solubility of the dyes, for example, metanil yellow, flavianic acid, and chrysophenine, in the presence of salts, e.g., sodium, potassium, and chloride salts, commonly occurring in human blood and hemoglobin, while the proteins natively present in lysed whole blood did not provide a similar effect on dye solubility. In order to overcome the slow solubility profile of the dyes in an albumin solution, the dyes were first dissolved in a solution containing a surfactant, such as Brij® 35. Therefore the dye was first dissolved in a surfactant solution before adding BSA. This mixture was subsequently added to the solution having hemoglobin, e.g., a hemoglobin concentrate. Any variation on the order of addition of surfactant, albumin and hemoglobin led to precipitation of the dye, reduced solubility, or a solubility profile that led to a processing time that was not commercially acceptable. The concentration of Brij 35® in the solution used to dissolve the dye prior to addition to the hemoglobin concentration, for example, is in the range of about 150 to 1500 g/L, preferably 750 to 1050 g/L, more preferably 900 g/L to ensure the concentration of Brij® 35 remained in excess of the critical micelle concentration. The concentration of BSA in this same dye concentrate solution, for example, is in the range of about 1 to 100 g/L, preferably 45 to 55 g/L, more preferably 50 g/L, or exceeds physiological concentrations of albumin.

The dyes chosen, according to the invention, mimic the spectrum of bilirubin in a patient sample and do not require a secondary algorithm, separate from those used to analyze clinical samples, to interpret the spectrum to produce meaningful clinical results. According to the invention, a pre-determined quantity of hemoglobin obtained, for example, from lysed red blood cells is added to the formulation of the quality control reference material. The quantity of hemoglobin added is sufficient to achieve total hemoglobin and hemoglobin fractions in a clinically relevant concentration range, i.e., physiological and pathological concentrations of hemoglobin and hemoglobin fractions (see Table I).

One or more dyes that are pre-dissolved in a solution containing an exogenous source of protein, are combined with a pre-determined quantity of hemoglobin to result in an absorption spectrum substantially similar to bilirubin over the wavelength range common to most CO-Oximetry systems.

According to the invention, a single dye or various combinations of dyes are chosen to best-match the absorbance of bilirubin (tBil) at various target analyte concentration ranges for total bilirubin (tBil) in a patent sample (0-40 mg/dL). For example, various dye combinations and their concentrations using, for example, metanil yellow, flavianic acid, and chrysophenine, are illustrated in Table II below. Other dyes and dye combinations are possible and the invention is not limited to the examples provided.

TABLE II

Comparison of dye combinations to best match tBil of patient plasma samples.

| Sample | tBil | Metanil Yellow | Flavianic Acid | Chrysophenine | |
|---|---|---|---|---|---|
| 1 | 13.0 | 0.2 | 0.1 | 0.1 | g L$^{-1}$ |
| 2 | 12.0 | 0.0 | 0.0 | 0.3 | g L$^{-1}$ |
| 3 | 33.8 | 0.0 | 0.0 | 1.0 | g L$^{-1}$ |
| 4 | 11.3 | 0.0 | 0.0 | 0.3 | g L$^{-1}$ |
| 5 | 8.5 | 0.0 | 0.1 | 0.2 | g L$^{-1}$ |
| 6 | 16.3 | 0.3 | 0.1 | 0.0 | g L$^{-1}$ |
| 7 | 25.0 | 0.0 | 0.0 | 0.7 | g L$^{-1}$ |
| 8 | 34.1 | 0.6 | 0.2 | 0.0 | g L$^{-1}$ |
| 9 | 17.5 | 0.0 | 0.0 | 0.4 | g L$^{-1}$ |
| 10 | 17.1 | 0.0 | 0.0 | 0.5 | g L$^{-1}$ |
| 11 | 25.6 | 0.1 | 0.0 | 0.6 | g L$^{-1}$ |
| 12 | 24.4 | 0.2 | 0.0 | 0.4 | g L$^{-1}$ |
| 13 | 16.7 | 0.3 | 0.1 | 0.1 | g L$^{-1}$ |
| 14 | 25.2 | 0.2 | 0.0 | 0.5 | g L$^{-1}$ |
| 15 | 29.4 | 0.5 | 0.1 | 0.2 | g L$^{-1}$ |
| 16 | 19.9 | 0.4 | 0.2 | 0.0 | g L$^{-1}$ |
| 17 | 13.0 | 0.0 | 0.0 | 0.3 | g L$^{-1}$ |

The dye selected, the quantity of each dye utilized, and the concentration of the dyes may be adjusted to reflect the desired level of tBil in the reference material as shown in Table II, where a single dye or combinations thereof can mimic the bilirubin spectra. The dye or dyes can be scaled to simulate any bilirubin concentration, in particular, clinically relevant concentrations of bilirubin (see, e.g., Table I).

The reference material provides sufficient precision and reproducibility required to effectively evaluate an instruments ability to measure total bilirubin (tBil) (See Table III below).

TABLE III

Precision of Total Bilirubin Reference Solutions across 6 GEM Premier 4000 Instruments

| | Chrysophenine | | | | | | Metanil Yellow | | | | | |
|---|---|---|---|---|---|---|---|---|---|---|---|---|
| | tHb | $O_2$Hb | COHb | MetHb | HHb | tBil | tHb | $O_2$Hb | COHb | MetHb | HHb | tBil |
| Inst 1 Mean | 15.6 | 97.2 | 1.6 | 0.4 | 0.8 | 18.0 | 15.6 | 97.2 | 1.6 | 0.5 | 0.7 | 18.9 |
| SD | 0.02 | 0.14 | 0.01 | 0.13 | 0.01 | 0.09 | 0.05 | 0.13 | 0.05 | 0.07 | 0.03 | 0.16 |
| Inst 2 Mean | 15.7 | 97.2 | 1.8 | 0.5 | 0.5 | 20.2 | 15.7 | 97.5 | 1.8 | 0.3 | 0.4 | 20.8 |
| SD | 0.03 | 0.12 | 0.05 | 0.14 | 0.02 | 0.11 | 0.02 | 0.16 | 0.06 | 0.11 | 0.05 | 0.02 |
| Inst 3 Mean | 15.5 | 97.2 | 1.8 | 0.7 | 0.3 | 20.1 | 15.5 | 97.4 | 1.9 | 0.6 | 0.2 | 20.7 |
| SD | 0.02 | 0.05 | 0.03 | 0.05 | 0.04 | 0.07 | 0.01 | 0.14 | 0.10 | 0.17 | 0.06 | 0.05 |
| Inst 4 Mean | 15.6 | 96.3 | 2.3 | 0.7 | 0.7 | 20.4 | 15.7 | 96.3 | 2.3 | 0.7 | 0.6 | 21.6 |
| SD | 0.02 | 0.07 | 0.03 | 0.05 | 0.01 | 0.25 | 0.03 | 0.12 | 0.04 | 0.05 | 0.10 | 0.08 |
| Inst 5 Mean | 15.6 | 96.6 | 2.2 | 0.8 | 0.5 | 19.4 | 15.6 | 96.8 | 2.3 | 0.6 | 0.3 | 20.3 |
| SD | 0.03 | 0.20 | 0.08 | 0.20 | 0.02 | 0.11 | 0.04 | 0.22 | 0.05 | 0.25 | 0.02 | 0.26 |
| Inst 6 Mean | 15.6 | 97.3 | 1.8 | 0.5 | 0.4 | 19.7 | 15.6 | 97.6 | 1.9 | 0.3 | 0.2 | 20.3 |
| SD | 0.05 | 0.10 | 0.02 | 0.09 | 0.01 | 0.23 | 0.02 | 0.22 | 0.04 | 0.09 | 0.10 | 0.52 |
| Overall Mean, mg $dL^{-1}$ ($\mu$M) | | | | | | 19.6 (336) | Overall Mean, mg $dL^{-1}$ ($\mu$M) | | | | | 20.4 (349) |
| Average Within Run SD, mg $dL^{-1}$ ($\mu$M) | | | | | | 0.16 (2.7) | Average Within Run SD, mg $dL^{-1}$ ($\mu$M) | | | | | 0.25 (4.3) |
| Instrument to Instrument SD, mg $dL^{-1}$ ($\mu$M) | | | | | | 0.88 (15.1) | Instrument to Instrument SD, mg $dL^{-1}$ ($\mu$M) | | | | | 0.89 (15.2) |

Each of the dyes used showed acceptable reproducibility. Through the use of this material it was found that one instrument (Instrument 1) reported significantly lower than the overall population by 10% (p<<0.01) and 9% (p<<0.01) for Chrysophenine and Metanil Yellow, respectively. Using these same instruments to run actual bilirubin samples it was found that Instrument 1 also recorded significantly below the normal population by 9% (p<<0.01), which supports the use of these reference solutions as an accurate simulation of instrument response to tBil.

In one embodiment according to the invention, the reference materials may be prepared as calibration materials or quality control materials to simultaneously calibrate tBil, total hemoglobin, and hemoglobin fractions by spectrometric means, and for blood gas, electrolytes, and various metabolites, for example, by enzymatic and electrochemical sensors.

Preferred reference material compositions, according to the invention, provide commercially acceptable stability in the range of about six weeks to three years, six weeks to one year, two months to two years, six months to one year, and two months, for example.

According to the invention, components included in the reference material do not interfere with electrochemical sensors of the analytical instrument in which the reference material is used. Accordingly, calibration or quality control of a variety of sensors and sensor types may be simultaneously conducted with the single reference material according to the invention. In addition to pre-determined quantities of dyes and hemoglobin, components of the reference material may include buffers, pre-determined quantities of analytes e.g., salts, glucose, lactate, and various gases, and other standard chemicals used in standard reference materials including preservatives, antimicrobials, and surfactants.

In one embodiment according to the invention, the reference material includes pre-determined quantities for pH, $PCO_2$, $PO_2$, $Na^+$, $K^+$, $Cl^-$, ionized calcium, glucose, lactate, total hemoglobin, hemoglobin fractions, and bilirubin, all of which are in quantities that are clinically meaningful, i.e., mimic physiological and pathological concentrations of these analytes. Reference materials according to the invention may be used for verifying the accuracy and reliability of instruments having sensors and spectrometers for measuring these analytes. A particular exemplification is described in Table IV below:

TABLE IV

Generic Formulation for Formulation of Final Product

| | Conc | Units |
|---|---|---|
| Deionized Water | A | L |
| Lysed Human RBCs | B | L |
| $O_2$Hb Intermediate | C | % |
| COHb Intermediate | D | % |
| Brij 35 | 900 | g $L^{-1}$ DI water |
| Albumin | 50 | g $L^{-1}$ DI water |
| HEPES (pH buffer) | 25 | mmol $L^{-1}$ |
| Sodium HEPES | 33 | mmol $L^{-1}$ |
| Sodium Lactate | 60 | mmol $L^{-1}$ |
| NAD | 0.7 | mmol $L^{-1}$ |
| Gentamicin | 3.33 | mg $L^{-1}$ |

Example Dye Concentration to Mimic Bilirubin (when used as individual dyes)

| | | | | |
|---|---|---|---|---|
| Simulated Bilirubin | 5 | 15 | 40 | mg $dL^{-1}$ |
| Chrysophenine | 67 | 200 | 540 | mg $L^{-1}$ |
| Metanil Yellow | 70 | 260 | 725 | mg $L^{-1}$ |

A, B, C, and D are varied to reach the desired tHb (deionized water (DI) and lysed RBC's) and hemoglobin fractions ($O_2$Hb and COHb intermediates) as described, for example, in U.S. Pat. No. 4,485,174, incorporated by reference herein. The dye concentrations listed are provided as an example, and can be adjusted to simulate intermediate bilirubin concentrations in the range of about 0-40 mg/dL (shown in Table IV, for example), as appropriate.

Figure 3:
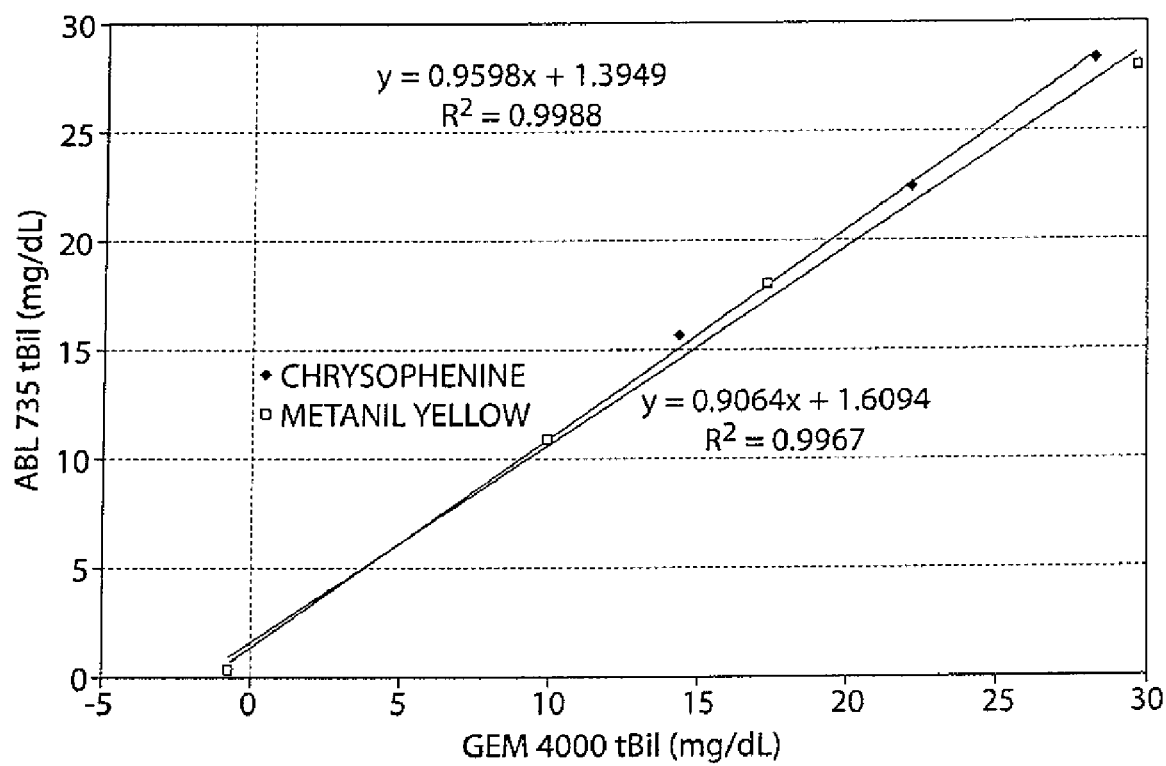
FIG. 3 illustrates the correlation between the GEM® Premier™ 4000 vs. ABL 735 analyzers with chrysophenine and metanil yellow dyes evaluated separately.

The compatibility of the formulation across multiple instruments that measure bilirubin, for example, GEM® Premier™ 4000 (Instrumentation Laboratory Company, Bedford, Mass.) or ABL 735 (Radiometer, Denmark) are illustrated in FIG. 3. Accordingly, the reference material according to the invention meets solubility requirements, mimics pre-determined concentrations of bilirubin that are clinically meaningful, may be used on multiple commercial analyzers, does not interfere with the analysis of tHb and its fractions, includes pre-determined clinically meaningful quantities of total hemoglobin and hemoglobin fractions, and does not interfere with sensors such as electrochemical sensors, all of which are provided in a single reference material that can be manufactured at a commercially acceptable cost. This product is stable for commercially acceptable time periods for example, as illustrated by the representative data in Table V below.

TABLE V

Stability evaluation of dyes in blood based matrix

| Days | tHb | $O_2Hb$ | COHb | HHb | MetHb | tBil |
|---|---|---|---|---|---|---|
| Chrysophenine (as measured at 2-8° C. on a GEM Premier ™ 4000) | | | | | | |
| 24 | 20.0 | 0.3 | 98.5 | 0.0 | 1.2 | 24.4 |
| 29 | 20.0 | 0.5 | 98.2 | 0.0 | 1.2 | 25.0 |
| 36 | 19.6 | 0.1 | 98.8 | 0.0 | 1.1 | 23.7 |
| 41 | 19.8 | 0.4 | 98.4 | 0.0 | 1.2 | 24.3 |
| 51 | 19.9 | 0.7 | 98.4 | 0.0 | 0.9 | 23.6 |
| 62 | 19.9 | 0.3 | 98.8 | 0.0 | 0.9 | 24.1 |
| Metanil Yellow (as measured at 2-8° C. on an ABL 735) | | | | | | |
| 0 | 14.9 | 96 | 1.4 | 0.4 | 2.4 | 28.0 |
| 64 | 15.1 | 95 | 1.2 | 0.2 | 3.6 | 28.9 |

Although the present invention has been described with reference to specific details, it is not intended that such details should be regarded as limitations upon the scope of the invention, except as and to the extent that they are included in the accompanying claims.

It will be apparent to these skilled in the art that various modifications and variations can be made to the above-described materials and methods of making without departing from the scope or spirit of the invention.

What is claimed is:

1. A reference material comprising:
   (i) a pre-determined clinically relevant quantity of total hemoglobin, or hemoglobin fractions, or combinations thereof sourced from hemolysed red blood cells;
   (ii) one or more dyes having an absorbance spectrum similar to the absorbance spectrum of pre-determined clinical concentrations of bilirubin, wherein said one or more dyes do not interfere with the absorbance of the pre-determined quantity of total hemoglobin or the pre-determined quantity of hemoglobin fractions;
   (iii) one or more buffers; and
   (iv) one or more salts.

2. The reference material of claim 1 further comprising,
   (v) bin analyte selected from the group consisting of glucose, lactate and calcium.

3. The reference material of claim 1 wherein said one or more salts is selected from the group consisting of Na, $K^+$ and $Cl^-$.

4. The reference material of claim 1 further comprising a component selected from the group consisting of a preservative, an antimicrobial and a surfactant.

5. The reference material of claim 4 where the surfactant is selected from the group consisting of polyoxyethylene (23) lauryl ether, polyoxyethylene (100) stearyl ether, polyoxyethylene fatty glyceride, and polyoxyethylene glycol tert-octylphenyl ether.

6. The reference material of claim 1 wherein said one or more dyes comprise chrysophenine.

7. The reference material of claim 1 wherein said one or more dyes comprise metanil yellow.

8. The reference material of claim 1 wherein said one or more dyes comprise flavianic acid.

9. The reference material of claim 1 wherein said one or more dyes comprise one or more of chrysophenine, metanil and flavianic acid.

10. The reference material of claim 9 wherein the concentration of chrysophenine is less than about 1000 mg/ml.

11. The reference material of claim 9 wherein the concentration of metanil yellow is less than about 1000 mg/ml.

12. The reference material of claim 9 wherein the concentration of flavianic acid is less than about 500 mg/ml.

13. The reference material of claim 1 wherein said clinically relevant quantity of total hemoglobin is in the range of 8-20 $gdl^{-1}$.

14. The reference material of claim 1 wherein said pre-determined clinical concentration of bilirubin is in the range of 0-30 mg $dl^{-1}$.

15. The reference material of claim 1 wherein said hemoglobin fractions comprises 60-98% oxyhemoglobin.

16. The reference material of claim 1 wherein said hemoglobin fractions comprises 0-20% carboxyhemoglobin.

17. The reference material of claim 1 wherein said hemoglobin fractions comprises 0-20% methemoglobin.

18. The reference material of claim 1 wherein a target analyte concentration of total hemoglobin in said reference material is in the range of about 0-25 mg $dl^{-1}$.

19. The reference material of claim 1 wherein a target analyte concentration of total bilirubin in said reference material is in the range of about 0-40 mg $dl^{-1}$.

20. The reference material of claim 1 wherein a target hemoglobin fraction in said reference material comprises a hemoglobin fraction selected from the group consisting of 0-100% oxyhemoglobin, 0-100% carboxyhemoglobin, and 0-100% methemoglobin.

* * * * *

UNITED STATES PATENT AND TRADEMARK OFFICE
CERTIFICATE OF CORRECTION

PATENT NO. : 8,304,244 B2
APPLICATION NO. : 13/349640
DATED : November 6, 2012
INVENTOR(S) : Pistorino et al.

Page 1 of 1

It is certified that error appears in the above-identified patent and that said Letters Patent is hereby corrected as shown below:

In the Claims

In Column 12, Line 16, in claim 10, delete "1000 mg/ml" and insert --1000 mg/L--, thereof In Column 12, Line 18, in claim 11, delete "1000 mg/ml" and insert --1000 mg/L--, thereof In Column 12, Line 20, in claim 12, delete "500 mg/ml" and insert --500 mg/L--, thereof In Column 12, Line 26, in claim 18, delete "mg dl-1" and insert --g dl-1--, thereof Signed and Sealed this
Twenty-sixth Day of November, 2013

Margaret A. Focarino
*Commissioner for Patents of the United States Patent and Trademark Office*